(12) United States Patent
Grob et al.

(10) Patent No.: US 8,989,875 B2
(45) Date of Patent: Mar. 24, 2015

(54) ELECTRODE APPARATUS

(75) Inventors: Timon Rutger Grob, Geldrop (NL); Sima Asvadi, Eindhoven (NL); Antonius Wilhelmus Maria De Laat, Den Dungen (NL); Judith Petra Huurdeman, Beek (NL); Dido Van Klinken, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 54 days.

(21) Appl. No.: 13/825,247

(22) PCT Filed: Sep. 19, 2011

(86) PCT No.: PCT/IB2011/054086
§ 371 (c)(1),
(2), (4) Date: May 9, 2013

(87) PCT Pub. No.: WO2012/038878
PCT Pub. Date: Mar. 29, 2012

(65) Prior Publication Data
US 2014/0148887 A1    May 29, 2014

Related U.S. Application Data

(60) Provisional application No. 61/384,747, filed on Sep. 21, 2010.

(51) Int. Cl.
*A61N 1/18* (2006.01)
*A61N 1/04* (2006.01)
*A61N 1/30* (2006.01)

(52) U.S. Cl.
CPC ............ *A61N 1/0492* (2013.01); *A61N 1/0408* (2013.01); *A61N 1/30* (2013.01)

USPC .......................................... 607/149; 607/153

(58) Field of Classification Search
None
See application file for complete search history.

(56) References Cited

U.S. PATENT DOCUMENTS

| | | | |
|---|---|---|---|
| 5,403,275 A | 4/1995 | Phipps | |
| 2004/0249432 A1* | 12/2004 | Cohen | 607/149 |
| 2007/0027411 A1* | 2/2007 | Ella et al. | 601/7 |
| 2008/0082153 A1* | 4/2008 | Gadsby et al. | 607/152 |
| 2008/0103462 A1* | 5/2008 | Wenzel et al. | 604/313 |
| 2008/0154230 A1 | 6/2008 | Subramony | |
| 2009/0264855 A1* | 10/2009 | Phipps | 604/501 |
| 2010/0030299 A1* | 2/2010 | Covalin | 607/46 |

FOREIGN PATENT DOCUMENTS

| | | |
|---|---|---|
| EP | 1905479 A1 | 4/2008 |
| WO | 0215974 A1 | 2/2002 |
| WO | 2005092430 A1 | 10/2005 |

* cited by examiner

*Primary Examiner* — Brian T Gedeon
*Assistant Examiner* — Ankit Tejani

(57) ABSTRACT

An electrode apparatus may be configured to provide electro-stimulation. The apparatus may include a current spreader and a spongeless volume disposed adjacent to the current spreader. The current spreader may be configured to spatially distribute electrical current across a stimulation area of a subject's skin. The spongeless volume may be configured to carry liquid gel or other fluent conductive substance that is configured to conduct electrical current between the current spreader and the stimulation area of the subject's skin to provide electro-stimulation.

15 Claims, 3 Drawing Sheets

Current density gradients 300

ELECTRODE APPARATUS

The invention relates to electrode apparatus configured to electrically couple to an area of skin of a subject in order to provide electro-stimulation and/or to obtain measurements.

Conventional electrodes for stimulation typically include hydrogels that facilitate electrical conduction between the electrodes and the skin of a subject. These hydrogels are solid jelly-like materials. Due to inconsistent current density (i.e., "hot spots") delivered to a stimulation area of a subject's skin from irregular skin contact and/or edge effects, these stimulation electrodes may often cause undesired tingling or burning sensation for subjects at the stimulation area.

Some existing measurement electrodes include a liquid gel encapsulated in a sponge for electrical coupling with the skin. Since the liquid gel is free-flowing, the sponge serves to keep an amount of the liquid gel in place between the electrode and the subject's skin. Such liquid-gel-in-sponge configurations may be sufficient for measurement applications. For stimulation applications, however, the decreased skin contact area of liquid-gel-in-sponge configurations can lead to similar undesired tingling for subjects as with hydrogels.

One aspect of the disclosure relates to apparatus configured to provide electro-stimulation. The apparatus may include a current spreader and a spongeless volume. The current spreader may be configured to spatially distribute electrical current across a stimulation area of a subject's skin. The spongeless volume may be disposed adjacent to the current spreader. The spongeless volume may be configured to carry a fluent conductive substance. The fluent conductive substance may be configured to conduct electrical current between the current spreader and the stimulation area of the subject's skin to provide electro-stimulation.

Another aspect of the disclosure relates to a method for providing electro-stimulation. The method may include disposing an electrode on a stimulation area of a subject's skin, wherein the electrode includes a current spreader and a spongeless volume carrying a fluent conductive substance. The method may include conducting electrical current between the current spreader and the stimulation area of the subject's skin via the fluent conductive substance, wherein the conducted electrical current is spatially distributed across the stimulation area of the subject's skin by the current spreader.

Yet another aspect of the disclosure relates to apparatus configured to provide electro-stimulation. The apparatus may include current spreading means and spongeless liquid gel carrying means. The current spreading means may be configured to spatially distribute electrical current across a stimulation area of a subject's skin. The spongeless liquid gel carrying means may be disposed adjacent to the current spreading means. The spongeless liquid gel carrying means may be configured to carry a fluent conductive substance. The fluent conductive substance may be configured to conduct electrical current between the current spreader and the stimulation area of the subject's skin to provide electro-stimulation.

These and other objects, features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn to scale. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Figure 1:
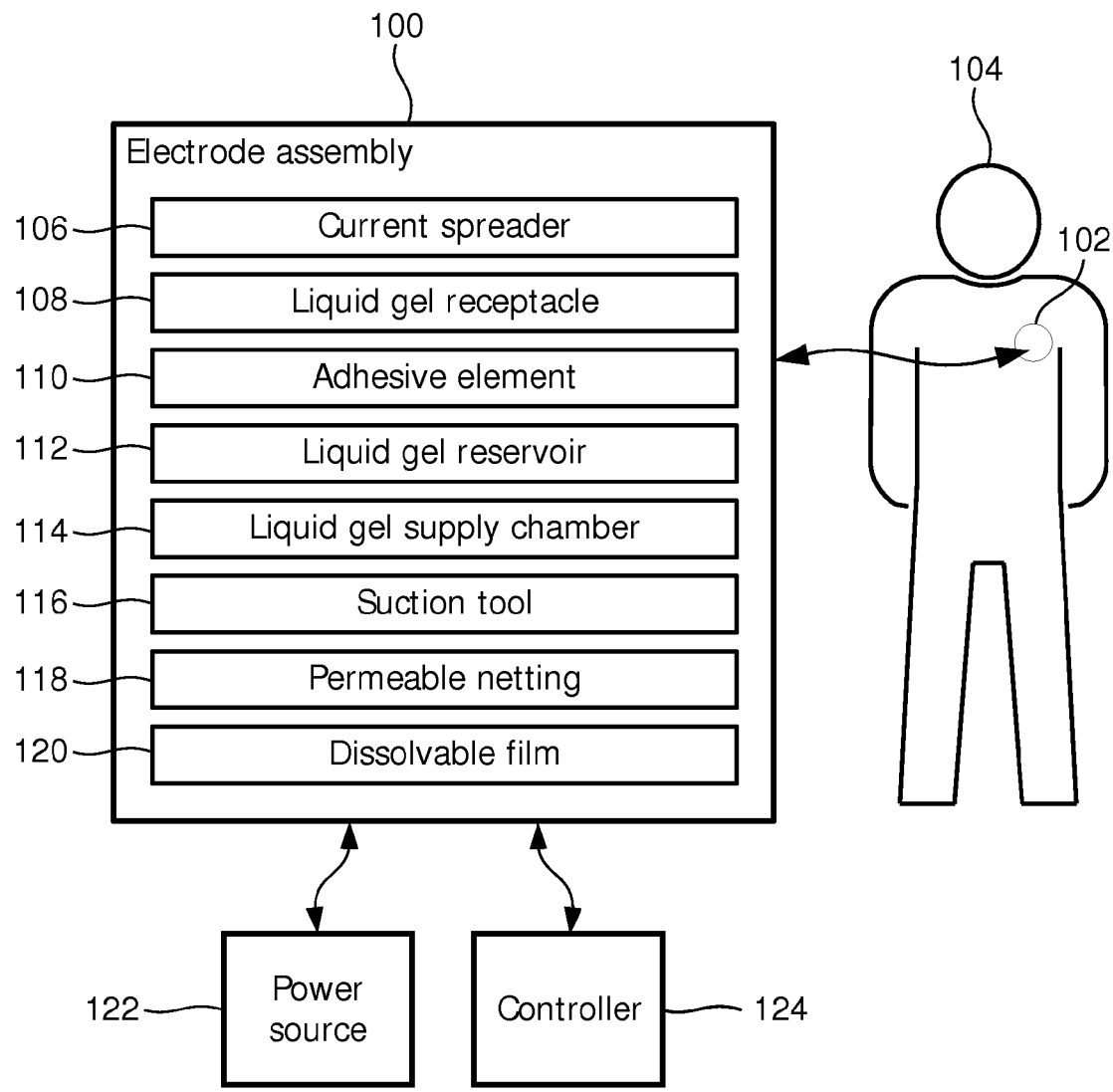
FIG. 1 illustrates an electrode assembly configured to electrically couple to an area of skin of a subject to provide electro-stimulation and/or to obtain measurements, in accordance with one or more embodiments of the invention.

FIG. 1 illustrates an electrode assembly 100 configured to electrically couple to an area of skin 102 of a subject 104 to provide electro-stimulation and/or to obtain measurements, in accordance with one or more embodiments of the invention. The area of skin 102 may be located at any position on the subject 104 where electro-stimulation and/or measurements are to be performed. Use of liquid gel or other fluent (i.e., capable of flowing) conductive substance may provide full skin contact and may decrease high current density hotspots. When conventional electrodes are prepared with gel only (i.e., not encapsulated in a sponge) the skin contact may be difficult to ensure, for example, due to seepage of the liquid gel away from the area of skin 102. The electrode assembly 100 may be configured to utilize liquid gel for electrical coupling to the area of skin 102 for stimulation and/or measurement, while ensuring proper skin contact.

As depicted in FIG. 1, the electrode assembly 100 may include one or more of a current spreader 106, a liquid gel receptacle 108, an adhesive element 110, a liquid gel reservoir 112, a liquid gel supply chamber 114, a suction tool 116, a permeable netting 118, a dissolvable film 120, and/or other components. The electrode assembly 100 may include, or be coupled to, a power source 122 configured to provide electrical power to one or more components of the electrode assembly 100. The electrode assembly 100 may include, or be coupled to, a controller 124 configured to control one or more components of the electrode assembly 100.

It should be appreciated that although components 106, 108, 110, 112, 114, 116, 118, and 120 are illustrated in FIG. 1 as being co-located within the electrode assembly 100, one or more of components 106, 108, 110, 112, 114, 116, 118, and/or 120 may be physically separate and distinct from the other components. The description of the functionality provided by the different components 106, 108, 110, 112, 114, 116, 118, and/or 120 described below is for illustrative purposes, and is not intended to be limiting, as any of components 106, 108, 110, 112, 114, 116, 118, and/or 120 may provide more or less functionality than is described. For example, one or more of components 106, 108, 110, 112, 114, 116, 118, and/or 120 may be eliminated. As another example, two or more of the components 106, 108, 110, 112, 114, 116, 118, and/or 120 may be combined into one or more single components with some or all of the functionalities attributed to the combined components.

The current spreader 106 may be configured to spatially distribute electrical current across a stimulation area (e.g., the area of skin 102) of the subject 104. Spatial distribution of electrical current may serve to avoid severe variances in current density delivered to the subject 104 during electro-stimulation. The current spreader 106 may include, for example, a metal plate, a conducting plate, and/or other apparatus configured to spatially distribute electrical current across an area. In exemplary embodiment, a conductive medium (e.g., liquid gel) may be disposed between the current spreader 106 and the skin of the subject 104 to enhance conduction of electrical current therebetween.

The liquid gel receptacle 108 may be disposed adjacent to the current spreader 106. The liquid gel receptacle 108 may be configured to carry liquid gel such that, when the electrode assembly 100 is applied to the area of skin 102 of the subject 104, liquid gel carried by the liquid gel receptacle 108 contacts the area of skin 102. According to exemplary embodiments, the liquid gel receptacle 108 does not contain a sponge to encapsulate liquid gel. In such embodiments, full contact is provided between the liquid gel carried by the liquid gel receptacle 108 and the area of skin 102 of the subject 104. The liquid gel is configured to conduct electrical current between the current spreader 106 and a stimulation area (e.g., the area of skin 102) of the subject 104 to provide electro-stimulation. According to some embodiments, the liquid gel may include dissolved salts, polyelectrolytes, other ionic species, salt-free liquid gel, and/or other fluent conductive substance. One example of a salt-free liquid gel is Spectra 360 Electrode Gel available from Parker Laboratories, Inc. of Fairfield, N.J. In some embodiments, the liquid gel includes a conditioning ingredient configured to locally increase the electrical conductivity of the skin of the subject 104 at the stimulation area. Examples of the conditioning ingredient include glycerin and/or other substances configured to enhance electrical properties of skin.

The adhesive element 110 may be configured to removably couple the electrode assembly 100 to the area of skin 102 of the subject 104 such that liquid gel carried by the liquid gel receptacle 108 contacts the area of skin 102. The adhesive element 110 may include any number of adhesive materials known in the art. It is noteworthy, however, that the adhesive element 110 should be capable of sufficiently adhering the electrode assembly 100 to the area of skin 102 to ensure consistent contact area of the liquid gel to preclude any hot spots (i.e., areas of high current density).

During some use scenarios, liquid gel carried by the liquid gel receptacle 108 may become at least partially depleted. For example, when the electrode assembly 100 is removed from packaging or when a cover is removed from the electrode assembly 100, some of the liquid gel carried by the liquid gel receptacle 108 may remain on the packaging or cover. As another example, when the electrode assembly 100 is applied to the area of skin 102 of the subject 104, some of the liquid gel carried by the liquid gel receptacle 108 may seep out of the liquid gel receptacle 108. Exemplary embodiments may be configured to prevent and/or compensate for depletion of liquid gel from the liquid gel receptacle 108, as described further below.

The liquid gel reservoir 112 may be in fluid communication with the liquid gel receptacle 108. The liquid gel reservoir 112 may be configured to store liquid gel. The liquid gel stored by the liquid gel reservoir 112 may be communicated to the liquid gel receptacle 108 by flowing through a structure configured to communicate fluids. Examples of such structures may include a channel, conduit, and/or other structure configured to communication fluids. Liquid gel stored by the liquid gel reservoir 112 may not directly contact the area of skin 102 or the current spreader 106, in some embodiments. The liquid gel reservoir 112 may be configured to provide additional liquid gel to the liquid gel receptacle 108 responsive to liquid gel in the liquid gel receptacle 108 being at least partially depleted. During application of the electrode assembly 100 to the subject 104, liquid gel in the liquid gel reservoir 112 may flow to the liquid gel receptacle 108, as a result of pressure applied to the electrode assembly 100 for proper adhesion, to replace any depleted liquid gel, according to some embodiments.

The liquid gel supply chamber 114 may be configured to store liquid gel. In some embodiments, the liquid gel supply chamber 114 may be included in the electrode assembly 100 and be in fluid communication with the liquid gel receptacle 108. In such embodiments, the liquid gel stored by the liquid gel supply chamber 114 may be communicated to the liquid gel receptacle 108 by flowing through a structure configured to communicate fluids. Examples of such structures may include a channel, conduit, and/or other structure configured to communication fluids. In other embodiments, the liquid gel supply chamber 114 may be physically separate and distinct from the electrode assembly 100. In such embodiments, the liquid gel supply chamber 114 may by configured to couple to the electrode assembly 100 to establish fluid communication with the liquid gel receptacle 108.

The suction tool 116 may be configured to reduce a fluid pressure (e.g., air pressure and/or liquid gel pressure) within the liquid gel receptacle 108. By reducing the fluid pressure within the liquid gel receptacle 108, liquid gel may be drawn from the liquid gel supply chamber 114 to the liquid gel receptacle 108. In some embodiments, the suction tool 116 may be included in the electrode assembly 100. In other embodiments, the suction tool 116 may be physically separate and distinct from the electrode assembly 100. According to one embodiment, the liquid gel supply chamber 114 and the suction tool 116 may be combined into a single device that is physically separate and distinct from the electrode assembly 100. Examples of the suction tool 116 may include a suction cup, a deformable bulb, and/or other apparatus configured to reduce a fluid pressure.

The permeable netting 118 may be configured to cover a portion of the liquid gel receptacle 108 by partially enclosing the liquid gel receptacle 108. That portion may be the portion of the liquid gel receptacle 108 that is closest to the subject 104 when the electrode assembly 100 is applied. The permeable netting 118 may include a permeable netting, a permeable membrane, and/or other flat or planar permeable materials. By way of non-limiting example, the permeable netting 118 may include a SN42 net available from Smith & Nephew Extruded Films Limited of East Yorkshire, England. The permeable netting 118 may be configured to communicate liquid gel therethrough from the liquid gel receptacle 108 to the area of skin 102 of the subject 104. In some embodiments, the permeable netting 118 may serve to hold liquid gel within the liquid gel receptacle 108 until the electrode assembly 100 is applied to the subject 104. Force applied to the electrode assembly 100 during application may cause liquid gel to travel through the permeable netting 118 so that the area of skin 102 is fully contacted by liquid gel. The permeable netting 118 may provide greater skin contact area, relative to existing liquid-gel-in-sponge configurations, to achieve a desirable decrease in current density hotspots.

The dissolvable film 120 may be configured to cover a portion of the liquid gel receptacle 108 by temporarily enclosing the liquid gel receptacle 108. That portion may be the portion of the liquid gel receptacle 108 that is closest to the subject 104 when the electrode assembly 100 is applied. The dissolvable film 120 may be configured to dissolve responsive to the dissolvable film 120 contacting the skin of the subject 104. When the dissolvable film 120 has dissolved, liquid gel in the liquid gel receptacle 108 may contact the area of skin 102 of the subject 104. The dissolvable film 120 may include one or more additives. Such additives may include a conditioning ingredient configured to locally increase the electrical conductivity of the skin of the subject 104, an ingredient that aids in adhesion of the electrode assembly 100 to the subject 104, and/or other additives.

It is noteworthy that some embodiments may include a sponge configured to encapsulate liquid gel (not depicted in FIG. 1), however, in those embodiments, such a sponge is not configured to contact the area of skin 102. For example, the electrode assembly 100 may include a sponge configured to encapsulate liquid gel that is disposed within the liquid gel receptacle 108, the liquid gel supply chamber 114, and/or other locations within the electrode assembly 100.

Figure 2:
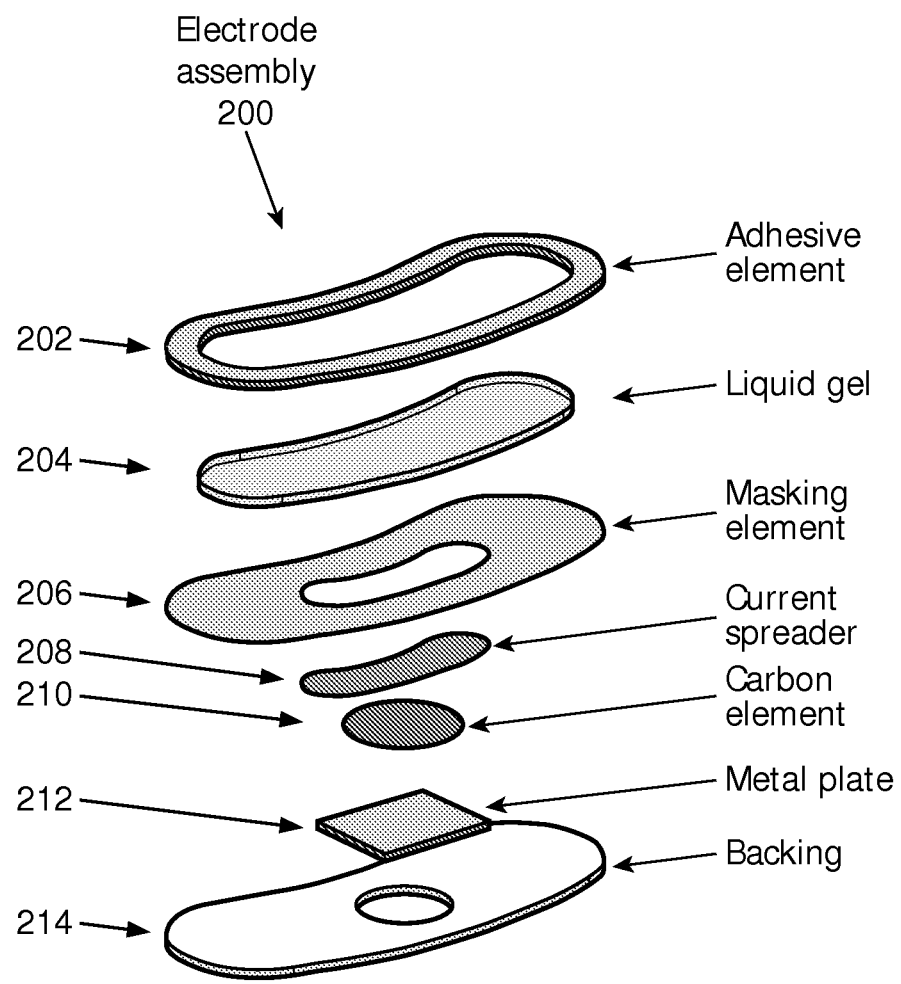
FIG. 2 illustrates an assembly view of an electrode assembly, in accordance with one or more embodiments of the invention.

FIG. 2 illustrates an assembly view of an electrode assembly 200, in accordance with one or more embodiments of the invention. In some embodiments, the electrode assembly 200 may include one or more components described in connection with the electrode assembly 100. As depicted in FIG. 2, the electrode assembly 200 may include an adhesive element 202, liquid gel 204, a masking element 206, a current spreader 208, a carbon element 210, a metal plate 212, backing 214, and/or other components. It should be appreciated that the depiction of the electrode assembly 200 in FIG. 2 is not intended to be limiting. For example, one or more of relative size, shape, assembly order, or other characteristics attributed to the adhesive element 202, the liquid gel 204, the masking element 206, the current spreader 208, the carbon element 210, the metal plate 212, and/or the backing 214 may be varied, according to some embodiments. Furthermore, one or more components of the electrode assembly 200 may be combined into a single component, and/or be omitted.

The adhesive element 202 may include some or all of the characteristics and/or functionalities attributed the adhesive element 110 described in connection with FIG. 1. In some embodiments, the adhesive element 202 and the masking element 206 may form a liquid gel receptacle (e.g., the liquid gel receptacle 108) configured to carry the liquid gel 204. The masking element 206 may be configured to electrically isolate a subject and/or other components of the electrode assembly 200 from the current spreader 208 and/or the liquid gel 204. The current spreader 208 may include some or all of the characteristics and/or functionalities attributed to the current spreader 106 described in connection with FIG. 1. The carbon element 210 may be configured to spatially distribute electrical current from the metal plate 212 to the current spreader 208. The carbon element 210 may be configured to provide adhesive properties to assure long-term electrical contact between the current spreader 208 and the metal plate 212. The metal plate 212 may be configured to receive electrical current from a power source (e.g., the power source 122). The metal plate 212 may be configured to provide removable magnetic coupling to a power source (e.g., the power source 122). It is noteworthy that some embodiment may include other mechanisms for physically coupling and/or electrical coupling to a power source such as a snap connector and/or other connectors. The backing 214 may be configured to support and/or carry components of the electrode assembly 200.

The electrode assembly 200 may include one or more other components not depicted in FIG. 2. According to some embodiments, a permeable netting (e.g., the permeable netting 118) and/or a dissolvable film (e.g., the dissolvable film 120) may be disposed above the adhesive element 202 to temporarily retain the liquid gel 204. In some embodiments, the backing 214 may include a reservoir (e.g., the liquid gel reservoir 112). In such embodiments, the current spreader 208 may include a correspondingly positioned hole providing fluid communication from the reservoir of the backing 214 to a liquid gel receptacle formed by the adhesive element 202 and the masking element 206.

Figure 3:
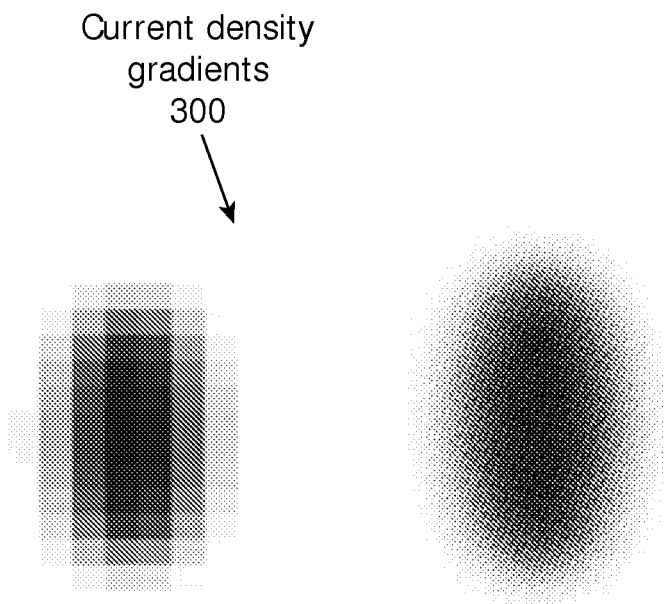
FIG. 3 illustrates current density gradients that may be provided by an exemplary electrode assembly to an area of skin of a subject, in accordance with one or more embodiments of the invention.

FIG. 3 illustrates current density gradients 300 that may be provided by an exemplary electrode assembly to an area of skin of a subject, in accordance with one or more embodiments of the invention. The grey scale intensity of the current density gradients 300 correspond to magnitude of current density, where dark regions represent higher current density. The edges of the current density gradients 300 may have lower current densities than the center regions. This may reduce effects of edges common in conventional electrodes, such as tingling during electro-stimulation. The shapes, sizes, and current density profiles of the current density gradients 300 illustrated in FIG. 3 are not intended to be limiting, as the current density gradients 300 may include other shapes, sizes, current density profiles, and/or other characteristics.

According to some embodiments, current density gradients (e.g. the current density gradients 300) may be provided by a current spreader (e.g., the current spreader 106 and/or current spreader 208). Conventional electrodes are generally made with current spreaders having a continuous conductivity over the bulk material, which may lead to current density issues at edges. Use of a current density spreader configured to provide a density gradient across a stimulation area of a subject's skin may reduce or eliminate current density hotspots at edges. In some embodiments, a current spreader may include conductive material patterned so as to provide a current density gradient. According to some embodiments, a current spreader may include a conductivity gradient where the current spreader is more conductive near the center relative to the edges of the current spreader such that a current density gradient may be provided. A current spreader may include a conductive material that is thicker near the center relative to the edges of the current spreader such that a current density gradient may be provided.

In accordance with some embodiments, current density gradients (e.g., the current density gradients 300) may be provided by liquid gel carried by the liquid gel receptacle 108 described in connection with FIG. 1. Conventional electrodes are generally made with gels (e.g., hydrogels and/or liquid gel encapsulated by a sponge) having continuous conductivity over the bulk material, which may lead to current density issues at edges. Use of liquid gel configured to provide a current density gradient across a stimulation area of a subject's skin may reduce or eliminate current density hotspots at edges. In some embodiments, liquid gel carried by the liquid gel receptacle 108 may include a conductive substance distributed across the volume of the liquid gel receptacle 108 so as to provide a current density gradient, wherein higher local concentrations of the conductive substance lead to higher current densities and vice versa. According to some embodiments, liquid gel carried by the liquid gel receptacle 108 may include a non-conductive component (e.g., non-conductive spheres) distributed across the volume of the liquid gel receptacle 108 so as to provide a current density gradient, wherein higher local concentrations of the non-conductive component lead to lower current densities and vice versa.

In some embodiments, current density gradients (e.g., the current density gradients 300) may be provided by netting partially enclosing the liquid gel receptacle 108. In such embodiments, the netting may have a lower hole density near the edges such that less liquid gel is delivered at the edges to the skin of a subject, thereby decreasing current density. Some embodiments include a dissolvable film having a conductive substance or a non-conductive component distributed across the area of the film so as to provide a current density gradient.

Figure 4:
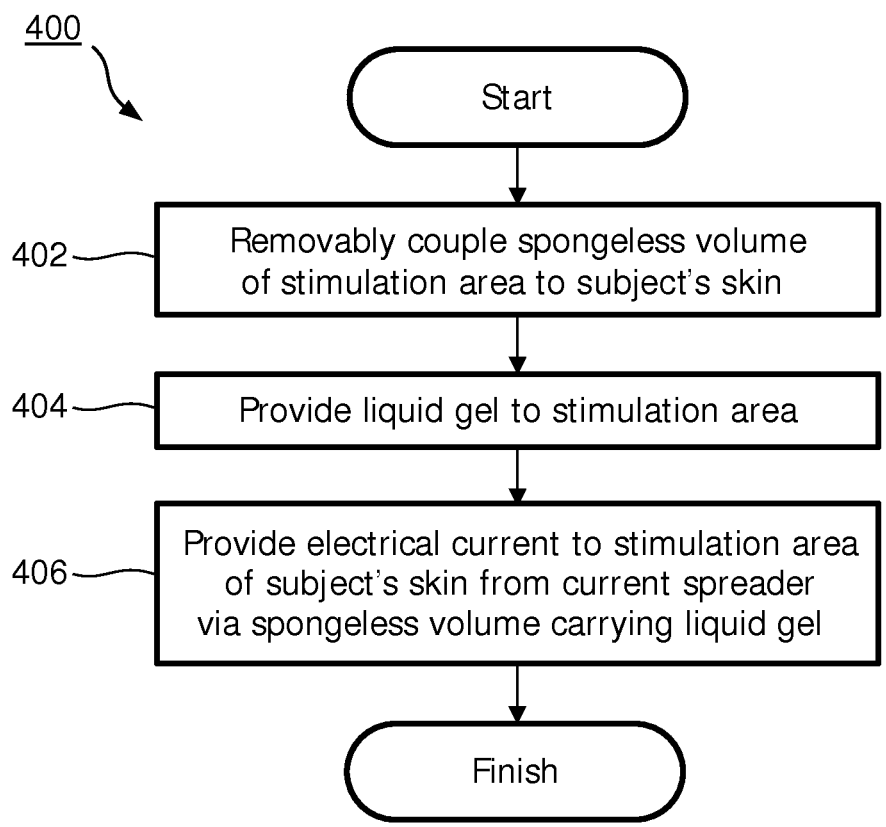
FIG. 4 is a flow chart illustrating a method for providing electro-stimulation, in accordance with one or more embodiments of the invention.

FIG. 4 is a flow chart illustrating a method 400 for providing electro-stimulation, in accordance with one or more embodiments of the invention. The operations of the method 400 presented below are intended to be illustrative. In some implementations, the method 400 may be accomplished with one or more additional operations not described, and/or without one or more of the operations discussed. Additionally, the order in which the operations of the method 400 are illustrated in FIG. 4 and described below is not intended to be limiting.

At an operation 402, a spongeless volume (e.g., the liquid gel receptacle 108) is removably coupled to a stimulation area of a subject's skin. Removable coupling may be achieved via an adhesive element (e.g., the adhesive element 110 and/or the adhesive element 202). The spongeless volume may carry liquid gel configured to conduct current from an adjacent current spreader to the stimulation area. Such liquid gel may include a conditioning ingredient to increase conductivity of the subject's skin at the stimulation area.

At an operation 404, liquid gel is provided to the stimulation area. In some embodiments, the liquid gel is provided to the stimulation area directly from the spongeless volume, from the spongeless volume via a netting (e.g., the permeable netting 118), from the spongeless volume via a dissolvable film (e.g., the dissolvable film 120), and/or by use of the liquid gel supply chamber 114 and the suction tool 116, as described in connection with FIG. 1. According to some embodiments, additional liquid gel may be provided to the stimulation area from the liquid gel reservoir 112, as described in connection with FIG. 1.

At an operation 406, electrical current is provided to the stimulation area of the subject's skin from the current spreader via the spongeless volume carrying liquid gel. The electrical current may be spatially distributed across the stimulation area. In accordance with some embodiments, operation 406 may include providing a current density gradient across the stimulation area of the subject's skin such that a current density at an edge of the stimulation area is less than a current density at an interior region of the stimulation area.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. Apparatus configured to provide electro-stimulation, the apparatus comprising:
   a current spreader configured to spatially distribute electrical current across a stimulation area of a subject's skin;
   a spongeless volume disposed adjacent to the current spreader and configured to carry conductive liquid gel, the conductive liquid gel configured to conduct electrical current between the current spreader and the stimulation area of the subject's skin to provide electro-stimulation;
   a liquid gel supply chamber configured to be in fluid communication with the spongeless volume and configured to store conductive liquid gel; and
   a suction tool configured to reduce a fluid pressure within the spongeless volume subsequent to the spongeless volume being removably coupled to the stimulation area of the subject's skin, such that the reduced fluid pressure within the spongeless volume causes the conductive liquid gel to be drawn from the liquid gel supply chamber to the spongeless volume.

2. The apparatus of claim 1, wherein the liquid gel supply chamber is further
   configured to provide additional conductive liquid gel to the spongeless volume responsive to the conductive liquid gel in the spongeless volume being at least partially depleted.

3. The apparatus of claim 1, further comprising either:
   (i) a permeable netting configured to cover a portion of the spongeless volume, and further configured to communicate the conductive liquid gel through the permeable netting from the spongeless volume to the stimulation area of the subject's skin; or
   (ii) a dissolvable film configured to cover a portion of the spongeless volume, and further configured to dissolve responsive to the dissolvable film contacting the subject's skin such that the conductive liquid gel in the spongeless volume contacts the stimulation area of the subject's skin.

4. The apparatus of claim 1, wherein
   the current spreader is further configured to provide a current density gradient across the stimulation area of the subject's skin such that peripheral current density of the stimulation area is less than central current density of the stimulation area.

5. The apparatus of claim 1, wherein the conductive liquid gel includes a conductive substance distributed across the spongeless volume such that peripheral current density of the stimulation are is less than central current density of the stimulation area.

6. A method for providing electro-stimulation, the method comprising:
   disposing an electrode on a stimulation area of a subject's skin, the electrode comprising a current spreader and a spongeless volume carrying a conductive liquid gel;
   removably coupling the spongeless volume to the stimulation area of the subject's skin using an adhesive element;
   storing conductive liquid gel in a liquid gel supply chamber in fluid communication with the spongeless volume;
   drawing the conductive liquid gel from the liquid gel supply chamber to the spongeless volume by reducing a fluid pressure within the spongeless volume using a suction tool; and
   conducting electrical current between the current spreader and the stimulation area of the subject's skin via the conductive liquid gel, the conducted electrical current being spatially distributed across the stimulation area of the subject's skin by the current spreader.

7. The method of claim 6, further comprising:
   providing additional conductive liquid gel from the liquid gel supply chamber to the spongeless volume responsive to the conductive liquid gel in the spongeless volume being at least partially depleted.

8. The method of claim 6, further comprising either:
(i) communicating the conductive liquid gel through a permeable netting from the spongeless volume to the stimulation area of the subject's skin; or
(ii) dissolving a dissolvable film responsive to the dissolvable film contacting the subject's skin such that the conductive liquid gel in the spongeless volume contacts the stimulation area of the subject's skin.

9. The method of claim 6, further comprising:
providing a current density gradient across the stimulation area of the subject's skin such that peripheral current density of the stimulation area is less than central current density of the stimulation area, wherein the current density gradient is provided by the current spreader.

10. The method of claim 6, further comprising:
providing a current density gradient across the stimulation area of the subject's skin such that peripheral current density of the stimulation area is less than central current density of the stimulation area, wherein the current gradient is provided by a conductive substance included in the conductive liquid gel, and wherein the conductive substance is distributed across the spongeless volume.

11. Apparatus configured to provide electro-stimulation, the apparatus comprising:
current spreading means configured to spatially distribute electrical current across a stimulation area of a subject's skin;
spongeless liquid gel carrying means disposed adjacent to the current spreading means and configured to carry a conductive liquid gel, the conductive liquid gel configured to conduct electrical current between the current spreader and the stimulation area of the subject's skin to provide electro-stimulation;
a liquid gel supply means in fluid communication with the spongeless liquid gel carrying means subsequent to the spongeless liquid gel carrying means being removably coupled to the stimulation area of the subject's skin such that the reduced fluid pressure within the spongeless liquid gel carrying means causes the conductive liquid gel to be drawn from the liquid gel supply means to the spongeless liquid gel carrying means.

12. The apparatus of claim 11, wherein the liquid gel supply means is further
configured to provide additional conductive liquid gel to the spongeless liquid gel carrying means responsive to the conductive liquid gel in the spongeless liquid gel carrying means being at least partially depleted.

13. The apparatus of claim 11, further comprising either:
(i) permeable means configured to cover a portion of the spongeless liquid gel carrying means, and further configured to communicate the conductive liquid gel through the permeable means from the spongeless liquid gel carrying means to the stimulation area of the subject's skin; or
(ii) dissolvable means configured to cover a portion of the spongeless liquid gel carrying means, and further configured to dissolve responsive to the dissolvable means contacting the subject's skin such that the conductive liquid gel in the spongeless liquid gel carrying means contacts the stimulation area of the subject's skin.

14. The apparatus of claim 11, wherein
the current spreading means is further configured to provide a current density gradient across the stimulation area of the subject's skin such that peripheral current density of the stimulation area is less than central current density of the stimulation area.

15. The apparatus of claim 11, wherein the conductive liquid gel includes a conductive substance distributed across the spongeless volume such that peripheral current density of the stimulation area is less than central current density of the stimulation area.

* * * * *